(12) United States Patent
Ellis et al.

(10) Patent No.: US 12,220,504 B1
(45) Date of Patent: Feb. 11, 2025

(54) GAS IRRADIATION APPARATUS

(71) Applicant: Environmental Technologies, LLC, Bakersfield, CA (US)

(72) Inventors: Stanley W. Ellis, Bakersfield, CA (US); Mitchell Caughron, Bakersfield, CA (US); Nicholas Acosta, Bakersfield, CA (US); James Lawrence LaBelle, Corona, CA (US)

(73) Assignee: Environmental Technologies, LLC, Bakersfield, CA (US)

( * ) Notice: Subject to any disclaimer, the term of this patent is extended or adjusted under 35 U.S.C. 154(b) by 0 days.

(21) Appl. No.: 18/763,962

(22) Filed: Jul. 3, 2024

(51) Int. Cl.
 *A61L 9/20* (2006.01)
 *A62B 18/02* (2006.01)

(52) U.S. Cl.
 CPC .............. *A61L 9/20* (2013.01); *A62B 18/02* (2013.01); *A61L 2209/111* (2013.01); *A61L 2209/12* (2013.01); *A61L 2209/14* (2013.01)

(58) Field of Classification Search
 None
 See application file for complete search history.

(56) References Cited

U.S. PATENT DOCUMENTS

| | | | |
|---|---|---|---|
| 6,303,086 B1 | 10/2001 | Heimer | |
| 8,153,058 B2 | 4/2012 | Araiza et al. | |
| 11,040,863 B2 | 6/2021 | Sonnenrein | |
| 11,161,062 B2 | 11/2021 | Johnson et al. | |
| 11,576,994 B1 | 2/2023 | Ellis et al. | |
| 11,629,872 B2 | 4/2023 | Carey et al. | |
| 2006/0165904 A1 | 7/2006 | Ohara | |
| 2007/0101867 A1* | 5/2007 | Hunter | A62B 23/02 96/224 |
| 2021/0299318 A1* | 9/2021 | Mullen | A61M 16/047 |
| 2022/0008601 A1 | 1/2022 | Wang | |
| 2022/0054666 A1* | 2/2022 | Phillips | A61M 16/201 |
| 2022/0218865 A1 | 7/2022 | Doyle et al. | |
| 2022/0290892 A1 | 9/2022 | Ghalebi et al. | |
| 2022/0347336 A1* | 11/2022 | Nanayakkara | A61L 9/20 |
| 2023/0227329 A1 | 7/2023 | Lu et al. | |

OTHER PUBLICATIONS

Rachel, P. Why Ultravilet Light Can't Pass Through Ordinary Glass, But Can Through Quartz Glass? MICQ Store. [online] [retrieved on Aug. 16, 2024]. pp. 1-7. https://micqstore.com/blogs/news/why-ultraviolet-light-can-t-pass-through-ordinary-glass-but-can-through-quartz-glass (Year: 2024).*

* cited by examiner

*Primary Examiner* — Jelitza M Perez
(74) *Attorney, Agent, or Firm* — James M. Duncan; Scanlon Duncan LLP

(57) ABSTRACT

A gas irradiation apparatus has a housing assembly having a gas inlet and a gas outlet. An irradiation chamber is contained within the housing, there the irradiation chamber has a first chamber, an adjacent second chamber, and an intermediate wall separating the first chamber from the second chamber. One or more conduits extend through the intermediate wall, which provide the exclusive flow path between the first chamber and the second chamber. A gas transfer fan is disposed within each conduit, with the gas transfer fans configured to induce flow between the first chamber and the second chamber. An array of light emitting diodes are configured to provide UVC light radiation into the irradiation chamber thereby irradiating any gas contained within the irradiation chamber.

21 Claims, 16 Drawing Sheets

GAS IRRADIATION APPARATUS

BACKGROUND OF THE INVENTION

The present invention generally relates to the treating gas to neutralize pathogens contained in the gas. More specifically, embodiments of the present invention relate to the neutralizing of pathogens contained in air inhaled by humans. Embodiments of the present invention may also be utilized for treating the exhalations of persons who may be infected with pathogens, including viruses, bacteria, fungi or other pathogens, where the exhalations may otherwise present a potential risk of harm to persons exposed to the exhalations. The recent and ongoing SARS-COV-2 coronavirus epidemic has illustrated the need for effective apparatus and methods which can provide safe breathing air for first responders, caregivers, and essential personnel. Such devices may be configured into a package which is relatively small, lightweight, easy to use, and having self-contained power means.

UVC light radiation ("UVC light") provides a method of using specific wavelengths of ultraviolet light to neutralize pathogens. The wavelengths of UVC light range from 100 to 280 nanometers. UVC light is germicidal, which means it deactivates the DNA of microorganisms such as bacteria, viruses, and other pathogens, which disrupt the ability of the microorganisms to multiply and cause disease.

A variety of devices are known which utilize UVC light for neutralizing pathogens. It is known that the level of neutralization of the pathogens is related to the exposure time of the pathogens to the UVC light, and the distance of the UVC light to the pathogens. An apparatus which provides effective exposure time and distance to multiple sources of UVC light to a gas stream potentially carrying pathogens is desirable. It is also desirable that embodiments of such an apparatus be configured into a portable, lightweight, and self-contained apparatus which may easily be carried and/or worn by first responders, caregivers, essential personnel, etc. It would also be desirable to have a device which may also be easily configured to neutralize pathogens in the exhalations of an infected person, effectively quarantining the infected person from caregivers, family members and the like. Embodiments of the present invention provide an answer to these needs.

SUMMARY OF THE INVENTION

Embodiments of the presently disclosed gas irradiation apparatus may purify incoming gas streams of pathogens and other biological material by utilizing UV LEDs. The UV LEDs have germicidal wavelengths of 100-400 nm, and typically in the range of 100-280 nm. The incoming air stream may first be filtered of air particulates, gases, vapors, and/or biological material by passing air through a high efficiency particulate air ("HEPA") filter to screen out particulates, gases, and vapors in addition to the pathogens.

An embodiment of the presently disclosed gas irradiation apparatus has a housing assembly and an irradiation chamber disposed within the housing assembly. A gas inlet extends through the housing assembly and into the irradiation chamber and a gas outlet extends from the irradiation chamber and out through the housing assembly. The irradiation chamber may have a volume ranging from 400-600 milliliters, which is sufficient for the tidal volumes of healthy average adult males and females. Peripheral devices utilized with the gas irradiation apparatus are a face mask unit with a hose which connections to the housing assembly and a backpack or carrying bag which provide for an individual to easily carry embodiments of the invention for personal use. The apparatus may be battery powered with a removable/rechargeable battery pack. A solar cell array may also be utilized to provide charging for the battery pack.

The irradiation chamber may have a first chamber connected to the gas inlet and an adjacent second chamber connected to the gas outlet, where the first chamber and second chamber are separated by an intermediate wall. Gas flow between the first chamber and the second chamber is exclusively limited to one or more conduits in the intermediate wall. A gas transfer fan is disposed within the conduit(s), where the gas transfer fan induces a flow of gas between the first chamber and the second chamber. One or more additional fans may be utilized to provide cooling and/or to provide a sufficient pressure differential as required for gas flow through the irradiation chamber, through connector tubing and to a face mask.

An array of light emitting diodes are configured to provide UVC light into the irradiation chamber. The array of light emitting diodes may comprise a first plurality of light emitting diodes configured to provide UVC light into the first chamber and a second plurality of light emitting diodes configured to provide UVC light into the second chamber. The first plurality of light emitting diodes may be disposed within a first heat sink plate positioned adjacent the first chamber and the second plurality of light emitting diodes may be disposed within a second heat sink plate positioned adjacent the second chamber. One or more auxiliary cooling fans may be positioned adjacent the first heat sink plate and the second heat sink plate to provide cooling around the light emitting diodes. The housing assembly may be configured to have a cooling air inlet through which cooling air is drawn in by cooling fans which direct the cooling air through internal ducting in the housing to circulate over the first heat sink plate, second heat sink plate, and the light emitting diodes.

The first chamber may have a first chamber wall having one or more fused silica quartz windows, with each of the light emitting diodes of the first plurality of light emitting diodes positioned adjacent to a fused quartz window. Likewise, the second chamber may have a second chamber wall having one or more fused silica quartz windows, with each of the light emitting diodes of the second plurality of light emitting diodes positioned adjacent to a fused quartz window.

The housing assembly may have a first housing member and a second housing member each having an open proximate end defined by a peripheral edge and a closed distal end opposite each open end. The housing assembly is configured such that when the first housing member and second housing member are attached together at the respective peripheral edges, a generally spherical or ellipsoidal encasement is formed which encloses the irradiation chamber. A gas inlet cavity portion is formed between the interior surface of the first housing member and the outside surface of the first chamber of the irradiation chamber wherein the gas inlet extends from the closed distal end of the first housing member and extends into the interior of the first chamber of the irradiation chamber. A gas outlet cavity portion is formed between the interior surface of the second housing member and the outside surface of the second chamber of the irradiation chamber wherein the gas outlet extends outwardly from the interior of the second chamber of the irradiation chamber to the closed distal end of the second housing member.

The attachment of the first housing member and the second housing member may be made with either a fused connection or a detachable connection. With the detachable connection, a double face seal may be disposed between the adjacent peripheral edges to provide the airtight seal.

The cavity portions of the housing assembly may be configured to receive modules which are respectively disposed into the cavity portions of the first housing member and the second housing member. A filter module may be disposed within the gas inlet cavity portion of the first housing member with the filter module connected to the gas inlet. A breathing hose module may be disposed within the gas outlet cavity portion of the second housing member with the breathing hose module connected to the gas outlet. Alternatively, to provide a reverse flow configuration, the breathing hose module may be disposed within the gas inlet cavity portion of the first housing member with the breathing hose module connected to the gas inlet. In this configuration, which may be utilized to purify the exhalations of a person infected with a disease or virus, an embodiment of a breathing hose module may be utilized which is configured to receive a filter, so that the exhalations are filtered prior to being introduced into the irradiation chamber. While a filter module may be disposed within the gas outlet cavity portion of the second housing member, the filter would be filtering gas which has already been irradiated and may therefore be omitted. The modules may be configured to be retained within the cavity portions of the housing members with fastening means, such as screws, or with fast connectors such as snap latches, draw latches, rotary draw latches, etc. with seal elements between the modules and cavity portions.

The filter module has a filter seat which is configured to receive a high efficiency particulate air filter (HEPA). The filter seat may be configured to channel incoming gas to both the gas inlet as well as to cooling gas intakes which direct cooling gas through ducts in the housing assembly and exterior of the irradiation chamber to flow over the heat sink plates and to exhaust through an exhaust gas outlet. Auxiliary cooling fans may be utilized to circulate the cooling gas. The filter, filter seat, the cooling gas intakes, and the ducts in the housing assembly and exterior of the irradiation chamber are configured so that gas which enters the cooling gas intakes is kept separate from gas which enters the interior of the irradiation chamber, such that in normal flow operation the only gas which flows into the gas outlet is gas which has been treated.

The filter module may have a filter module cover which may be pivotally or otherwise attached to the filter module. The filter module cover is configured to close and secure the filter element in place within the filter seat and allow an incoming flow of gas to flow through the filter element and into the gas inlet. A sensor may be utilized to detect the correct placement of the filter within the filter seat. For example, the filter element may have an embedded magnet which activates a Reed switch to confirm the filter is in place. The filter element may further comprise a keyed feature to insure the filter have inserted in correct position for air flow. The filter module cover may utilize either a mechanical latching mechanism or a closure magnet to maintain the filter module cover in a closed position. A sensor may also be utilized to provide confirmation that the filter module cover is in the closed position. For example, the filter module cover may have a detection magnet.

The breathing hose module has a breathing hose receptacle configured to receive a hose for a breathing mask. The breathing hose receptacle may have a hose access cover which provides protection from the ingress of water and debris. The hose access cover may be biased to return to a closed position upon the removal of a hose from the breathing hose receptacle. When the apparatus is in a normal flow configuration, with treated gas exiting through the gas outlet to a breathing hose and mask, an exhaust airway seal between the housing assembly and the irradiation chamber prevents any of the cooling gas to exit through the gas outlet. A hose attachment member may comprise a molded hose elbow having an integrated seal at its base which mates with the breathing hose receptacle. The base may have an integrated magnet which attaches to a mating steel ring contained within the breathing hose receptacle. The magnet may be utilized in conjunction with a sensor which determines whether a breathing hose has been attached to the breathing hose receptacle. The molded hose elbow may have an exterior end for receiving an industry standard 15 millimeter CPAP hose. The hose attachment member may be configured to provide 360 degrees of rotation within the breathing hose receptacle. A silicon/elastomer seal provides an airtight connection between the base of the hose attachment member and the breathing hose receptacle.

As discussed above, a reverse flow operation may be achieved by disposing the breathing hose module within the cavity portion of the first housing member with the breathing hose module connected to the gas inlet and, if desired, the filter module may be disposed within the cavity portion of the second housing member with the filter module connected to the gas outlet. Alternatively, reverse flow operation may be achieved by changing the direction of a fan or other pressure differential apparatus, in which case the flow of gas enters the irradiation chamber through the "gas outlet" into the irradiation chamber and flows out of the "gas inlet" and released to the atmosphere.

Embodiments of the gas irradiation apparatus may utilize an onboard processor which provides control of the various onboard systems, including the light emitting diodes, the fan system, the cooling system, the filter detector, the filter module cover detector, and the breathing hose attachment sensor. The onboard processor may be placed within a cavity between an exterior wall of the irradiation chamber and the interior wall of the housing assembly.

DETAILED DESCRIPTION OF THE INVENTION

Figure 2:
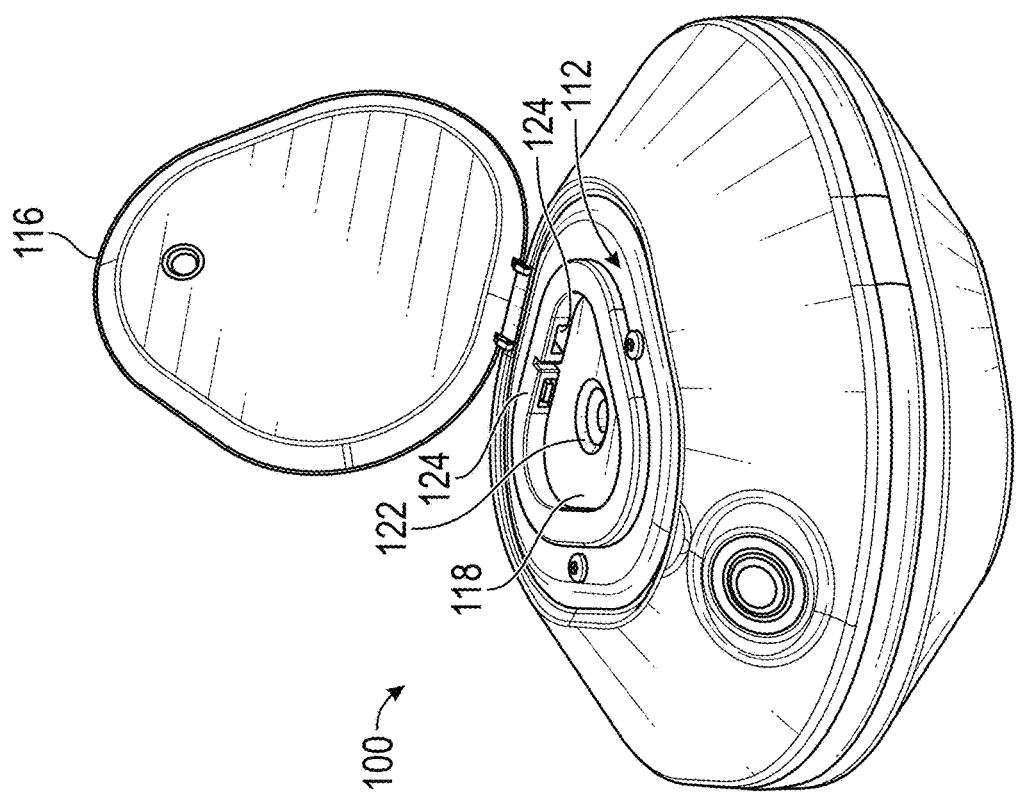
FIG. 2 shows a perspective view of the embodiment of FIG. 1 with a filter module cover in an open position.
Figure 1:
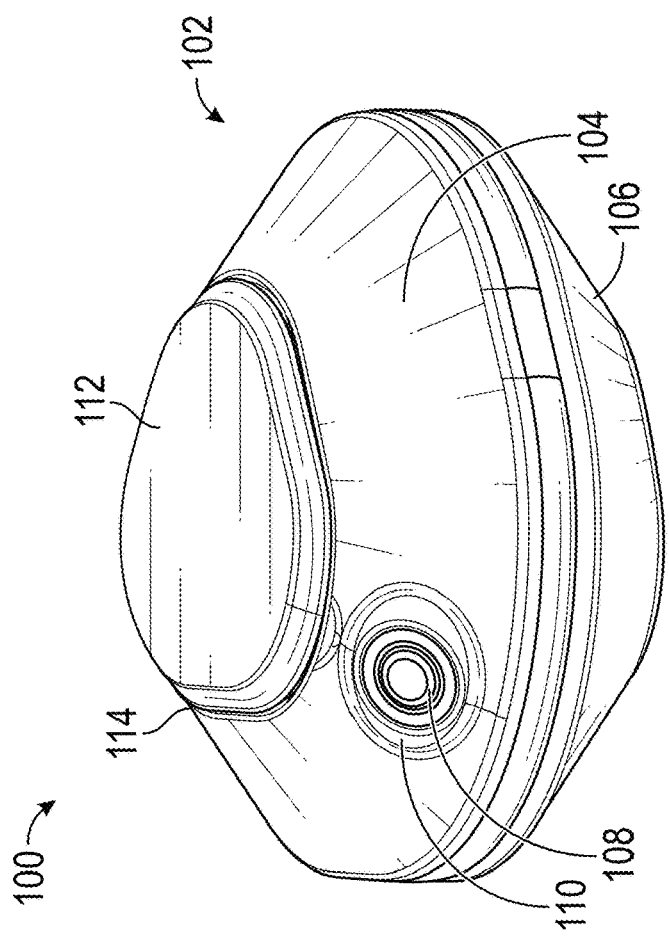
FIG. 1 shows a perspective view of an embodiment of the presently disclosed gas irradiation apparatus with a filter module positioned adjacent a gas inlet of the apparatus.

Referring now to the Figures, FIG. 1 shows a perspective view of an embodiment of the presently disclosed irradiation apparatus 100, with the view directed toward the gas intake side of the apparatus For the embodiment depicted in FIGS. 1-2, a filter module 112 is positioned so that incoming gas is directed through the filter module.

Figure 8:
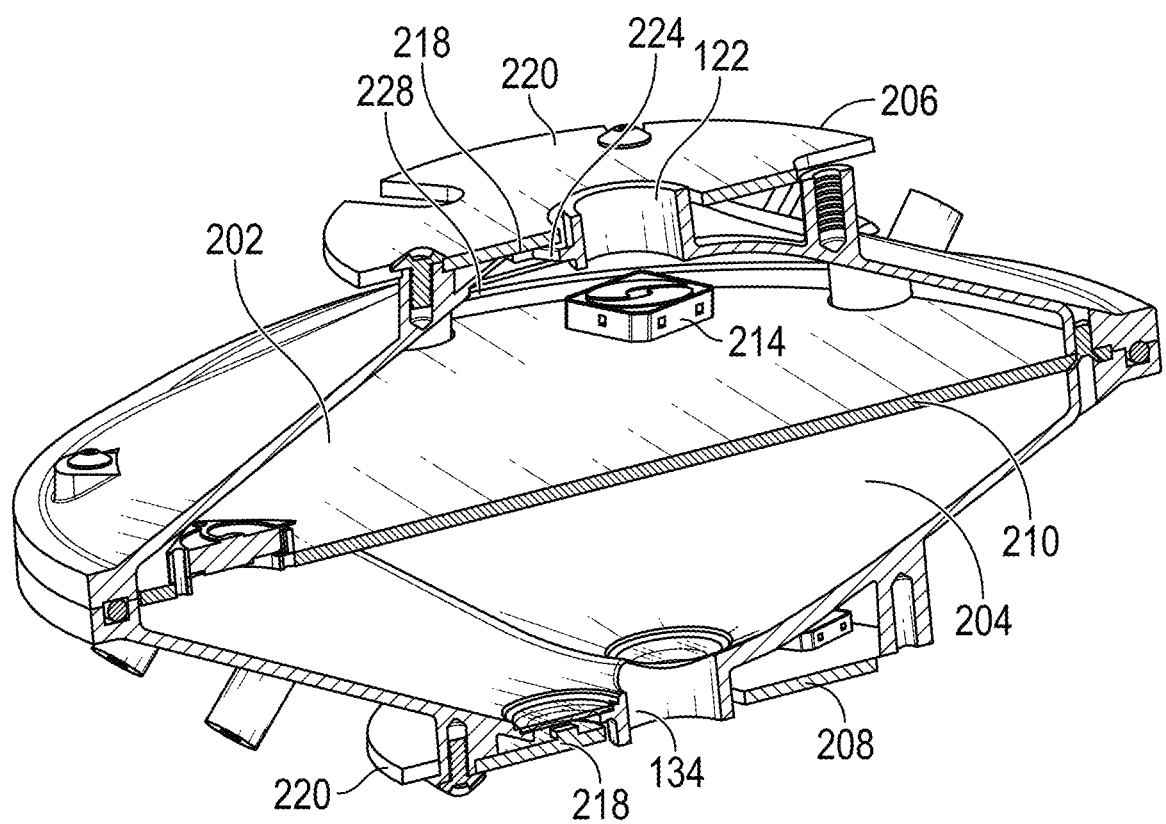
FIG. 8 shows a sectioned view of an embodiment of a reaction chamber of the presently disclosed gas irradiation apparatus with the first housing member and the second housing member removed.
Figure 9:
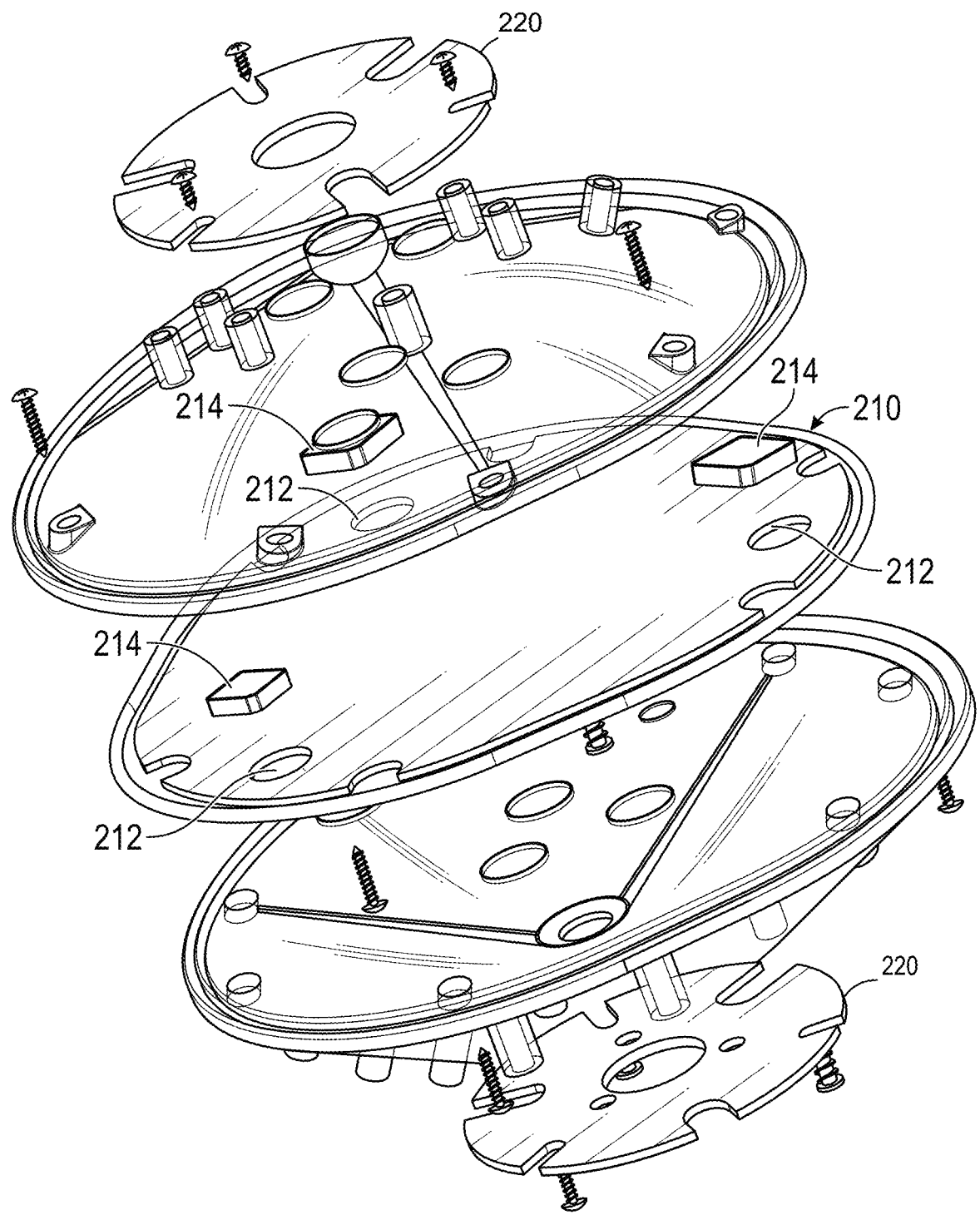
FIG. 9 shows an exploded view of the reaction chamber.
Figure 9A:
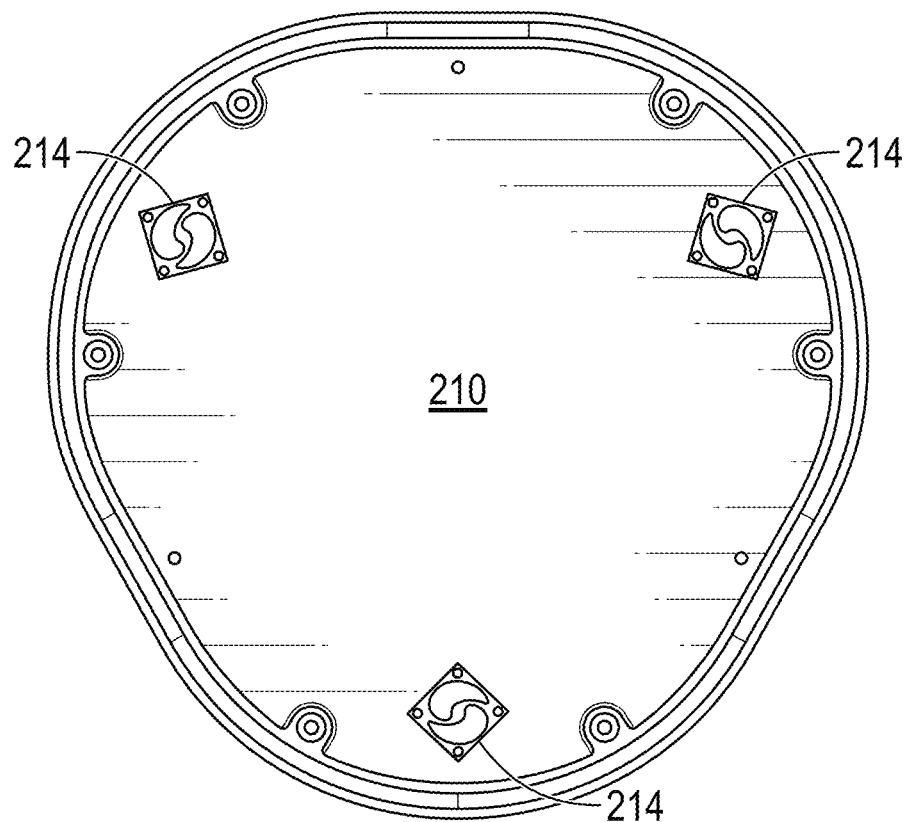
FIG. 9A shows an embodiment of an intermediate wall of the reaction chamber which separates the first chamber from the second chamber, showing the fan placement on the exhaust side of the wall.

An embodiment of the irradiation apparatus 100 may have a housing assembly 102 having a first housing member 104 and a second housing member 106. The housing assembly 102 is configured such that when the first housing member 104 and second housing member 106 are attached together, a generally spherical or ellipsoidal encasement is formed which encloses an irradiation chamber assembly 200 as depicted in FIGS. 8-9. Irradiation chamber assembly 200 may be configured to have a volume suitable for the average human lung capacity, typically ranging from 400 to 600 milliliters.

Figure 19:
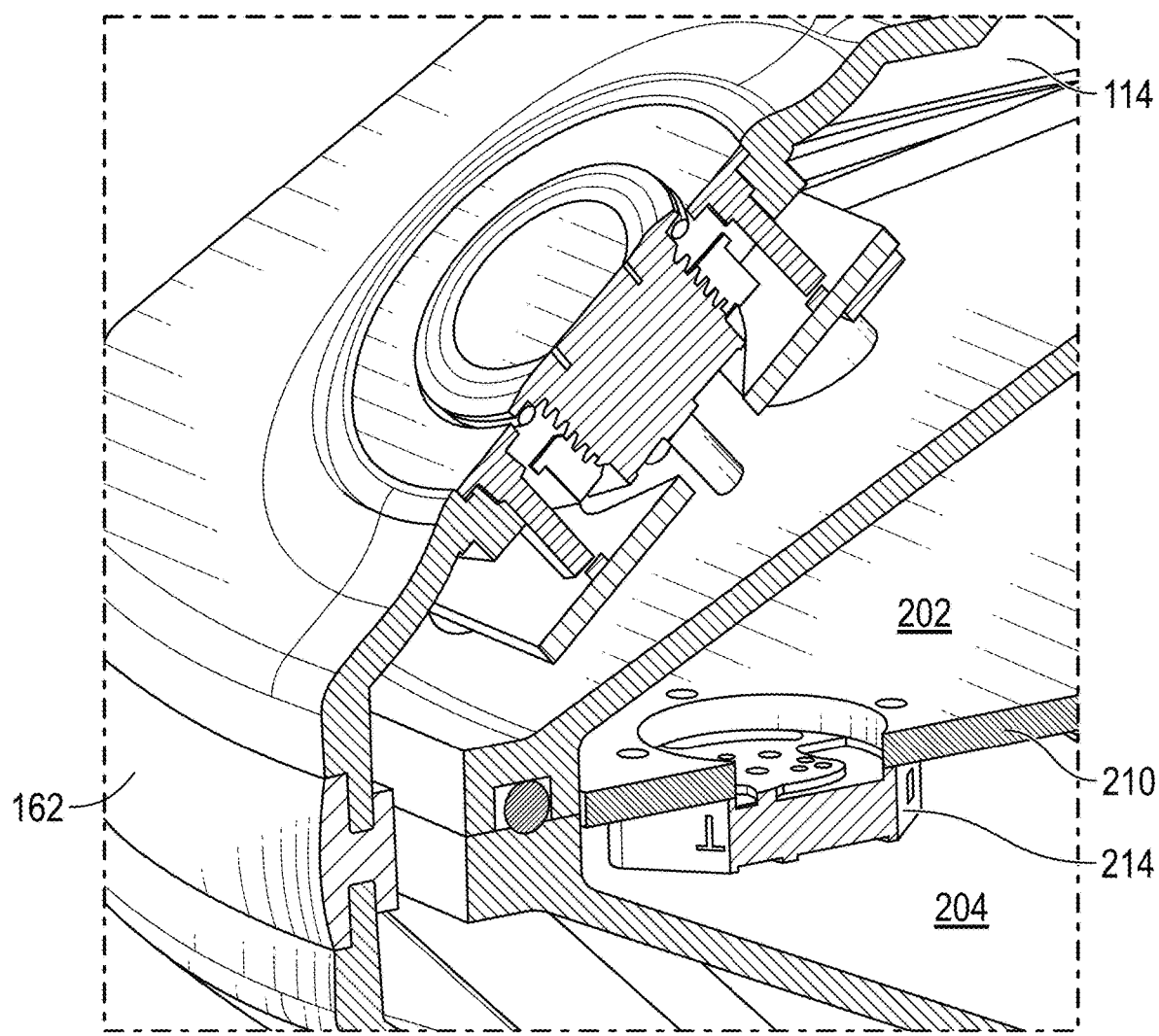
FIG. 19 shows how an embodiment of the apparatus may be activated with a momentary on/off switch with illumination capability.

The irradiation apparatus 100 may be activated by a momentary on/off switch 108 which may have an injection molded light ring 110 which is bonded to housing assembly 102, such as to first housing member 104 as shown in FIG. 1 and shown in detail in FIG. 19. FIG. 1 also shows a filter module 112 inserted into a gas inlet cavity portion 114 of first housing member 104.

FIG. 2 shows irradiation apparatus 100 with filter element cover 116 in an open position to provide access to filter seat 118. Filter element cover 116 may be pivotally attached to filter module 112 as shown in FIG. 2. Filter seat 118 is positioned such that a HEPA filter 120, as shown in FIG. 7, may be placed in position over gas inlet 122.

Figure 2A:
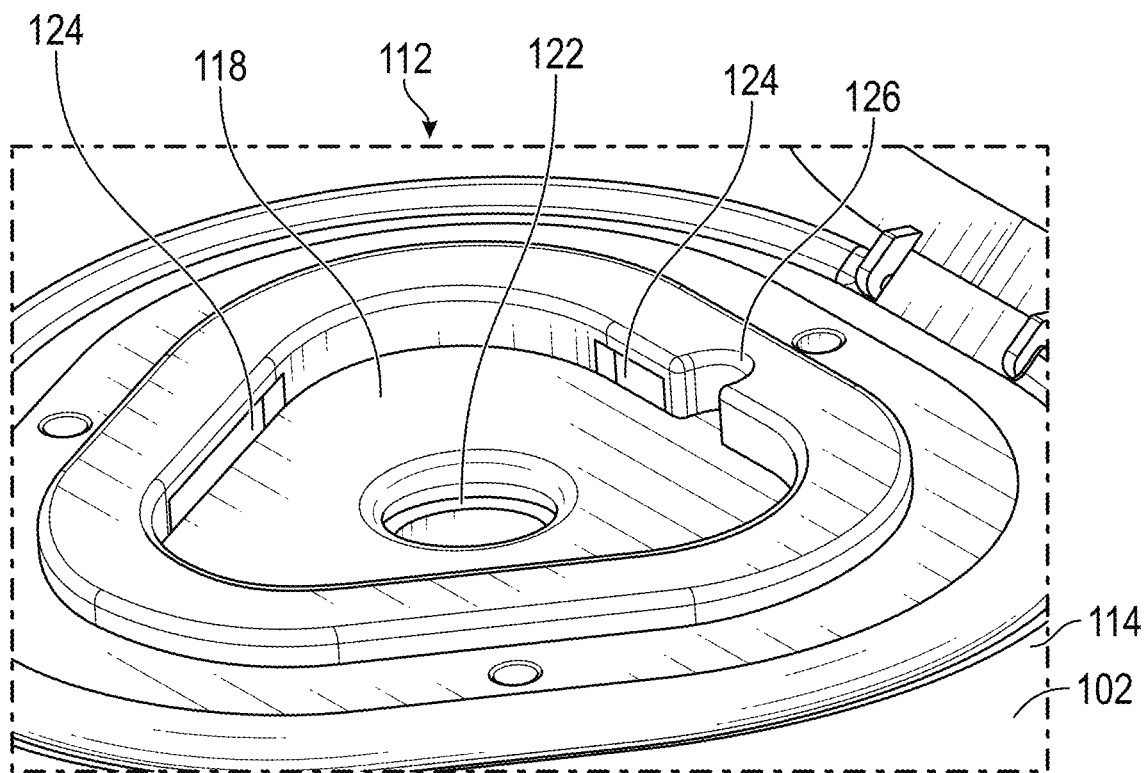
FIG. 2A shows a close-up view of an embodiment of the filter module positioned within a cavity portion of the housing assembly.
Figure 7:
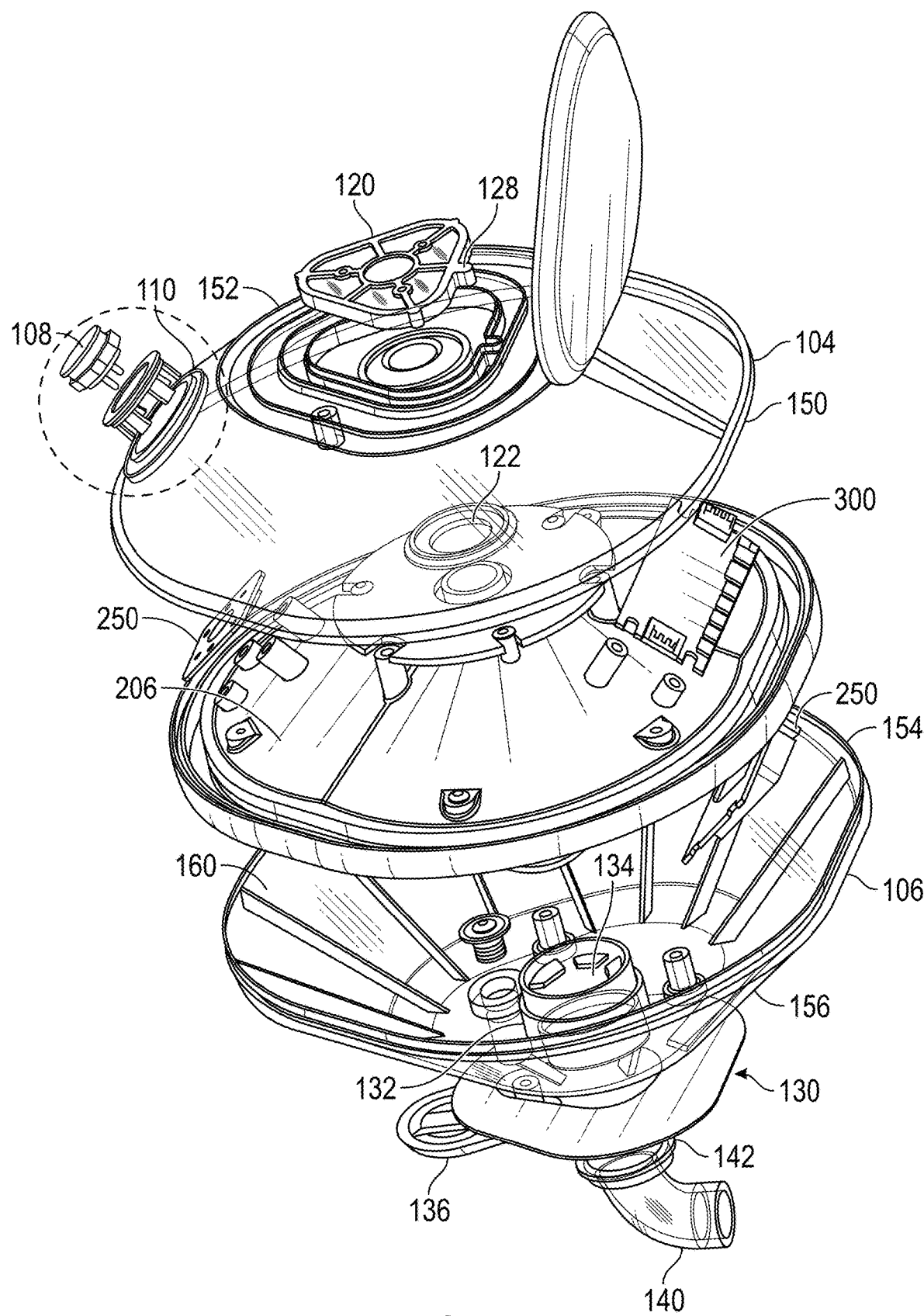
FIG. 7 shows an exploded view of an embodiment of the presently disclosed gas irradiation apparatus.

Filter seat 118 may have cooling gas intakes 124 through which cooling air is drawn in by cooling fans 250, as shown in FIG. 7, to channel flow over the internal components of the apparatus to provide cooling. FIG. 2A shows a close-up view of the filter seat 118, showing how module 112 may be disposed within gas inlet cavity portion 114 of the housing assembly 102. As shown in FIG. 2A, the filter seat 118 may have a keyway 126 which corresponds with a key feature 128 of HEPA filter 120 to insure proper positioning of the filter. Key feature 128 may have an embedded magnet which activates a electronmechanical switch to detect whether the filter 120 is seated within the filter seat 118 and properly positioned. When closed, filter element cover 116 secures filter 120 in place while allowing incoming gas to flow into the filter.

Figure 3:
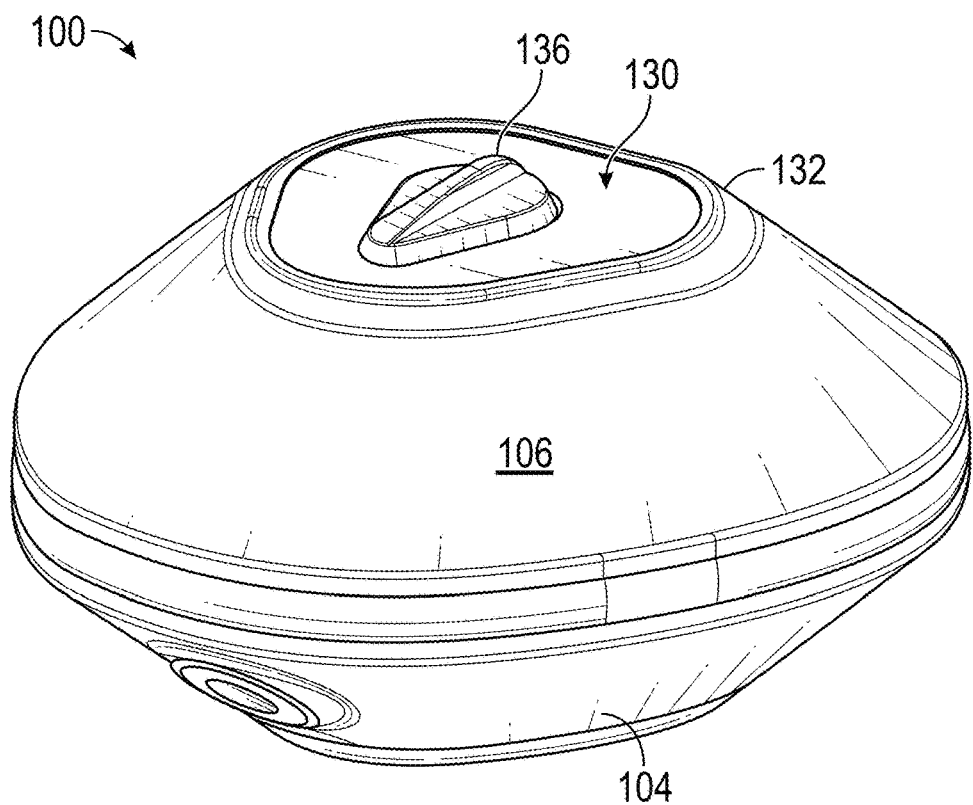
FIG. 3 shows a perspective view of an embodiment of the presently disclosed gas irradiation apparatus with a hose module positioned adjacent a gas outlet of the apparatus with a protection door over a a breathing hose receptacle in a closed position.
Figure 4:
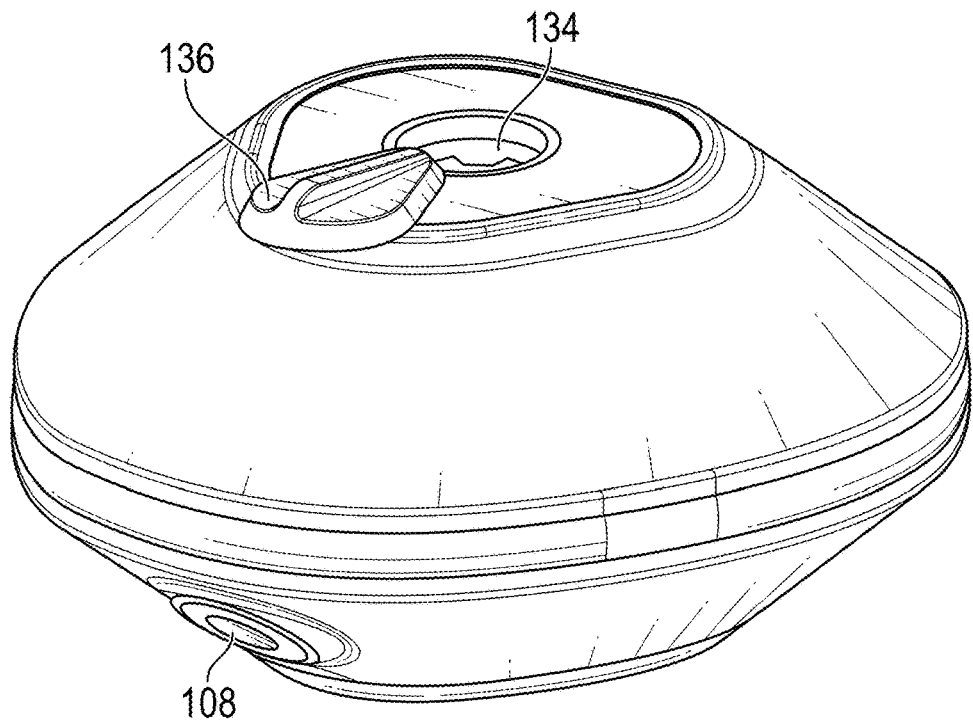
FIG. 4 shows a perspective view of the embodiment of FIG. 3 with the protection door over the breathing hose receptacle in an open position.

FIG. 3 shows a perspective view of an embodiment of the presently disclosed irradiation apparatus 100 with the view directed toward the gas outlet side of an embodiment of the apparatus. For the embodiment depicted in FIGS. 3-4, a beathing hose module 130 is positioned so that outflowing treated gas is directed out through the hose module. Hose module 130 may be inserted into a gas outlet cavity portion 132 of second housing member 106. The breathing hose module 130 has a breathing hose receptacle 134 which functions as a gas outlet when the apparatus is operated in a normal flow configuration. Breathing hose receptacle 134 is configured to receive a hose (not shown) for a breathing mask.

Figure 12:
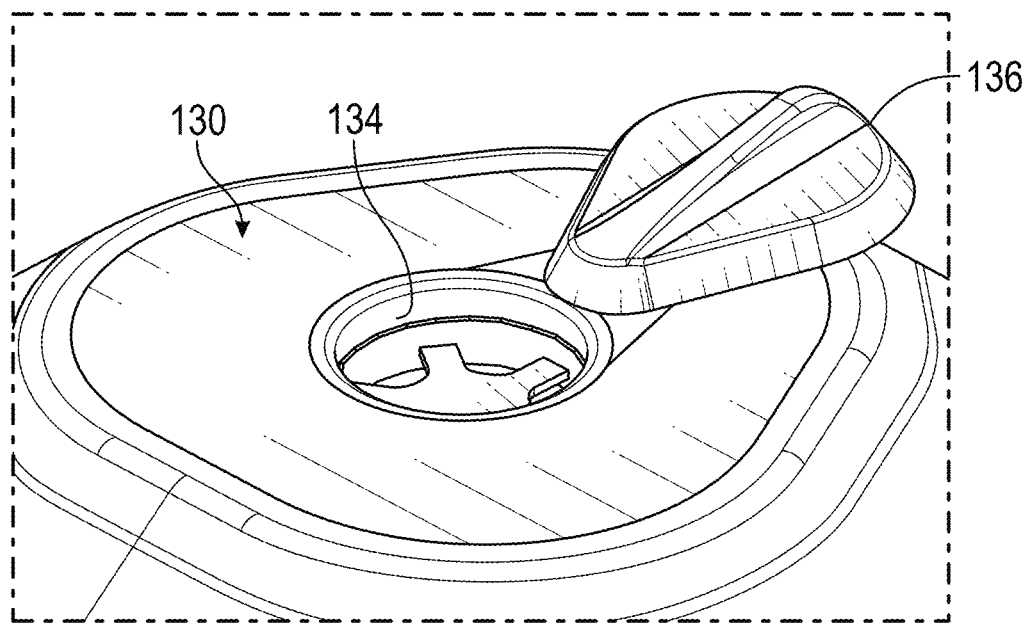
FIG. 12 shows detailed view of an embodiment of a protection door which may be utilized with an embodiment of a breathing hose module.
Figure 13:
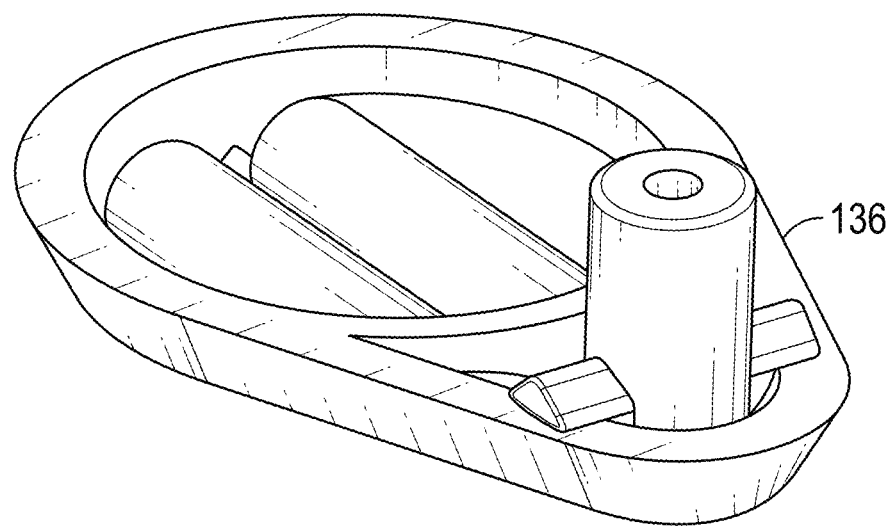
FIG. 13 shows a view of the underside of the protection door depicted in FIG. 10.
Figure 14:
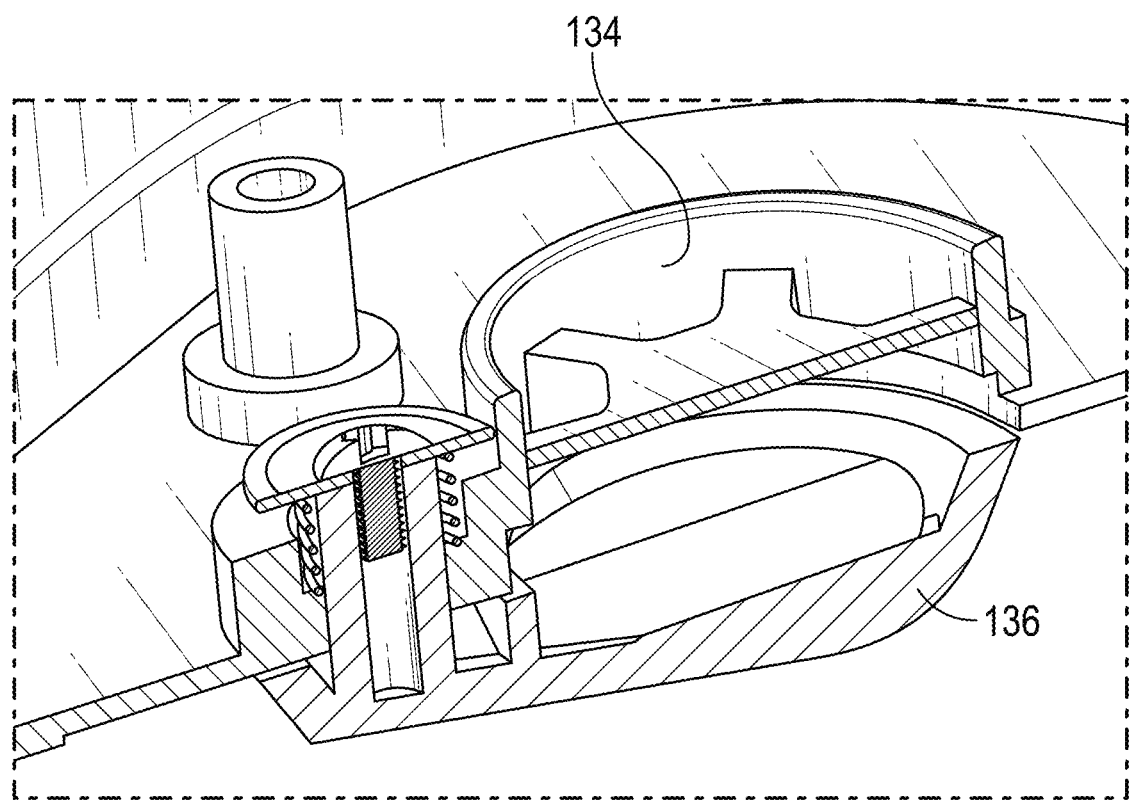
FIG. 14 shows a sectioned interior view of the protection door depicted in FIGS. 10-11, showing how an embodiment of the protection door may be positioned between a closed or lowered position to an open and raised position utilizing a biasing spring, thereby providing access to an outlet below the protection door.
Figure 17:
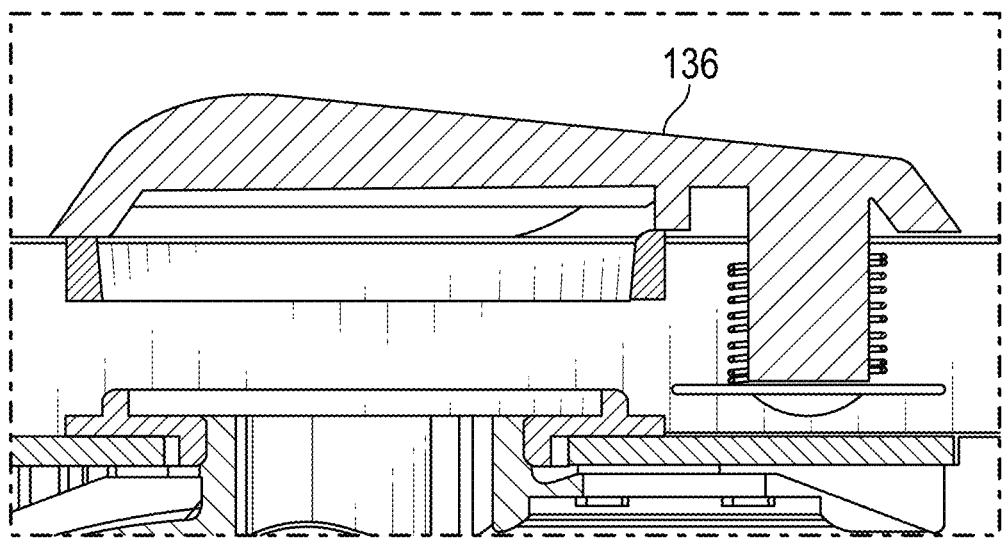
FIG. 17 shows how the protection door may seal against a hose inlet gasket to provide moisture ingress protection.

The breathing hose receptacle 134 of breathing hose module 130 may have a hose access cover or protection door 136 which provides protection from the ingress of water and debris. As shown in FIG. 12, the protection door 136 may be manually positionable and may also be biased to return to a closed position upon the removal of a hose from the breathing hose receptacle 134. FIG. 13 shows a detailed view of the underside of protection door 136 showing that it may utilize a rise cam feature that lifts as the cover is rotate open and then lowered at 180 degrees of rotation. As further shown in FIGS. 14 and 17, the protection door 136 is spring loaded so that is biased into a closed position. The doo 136 is designed to prevent water and debris from entering into the apparatus.

Figure 5:
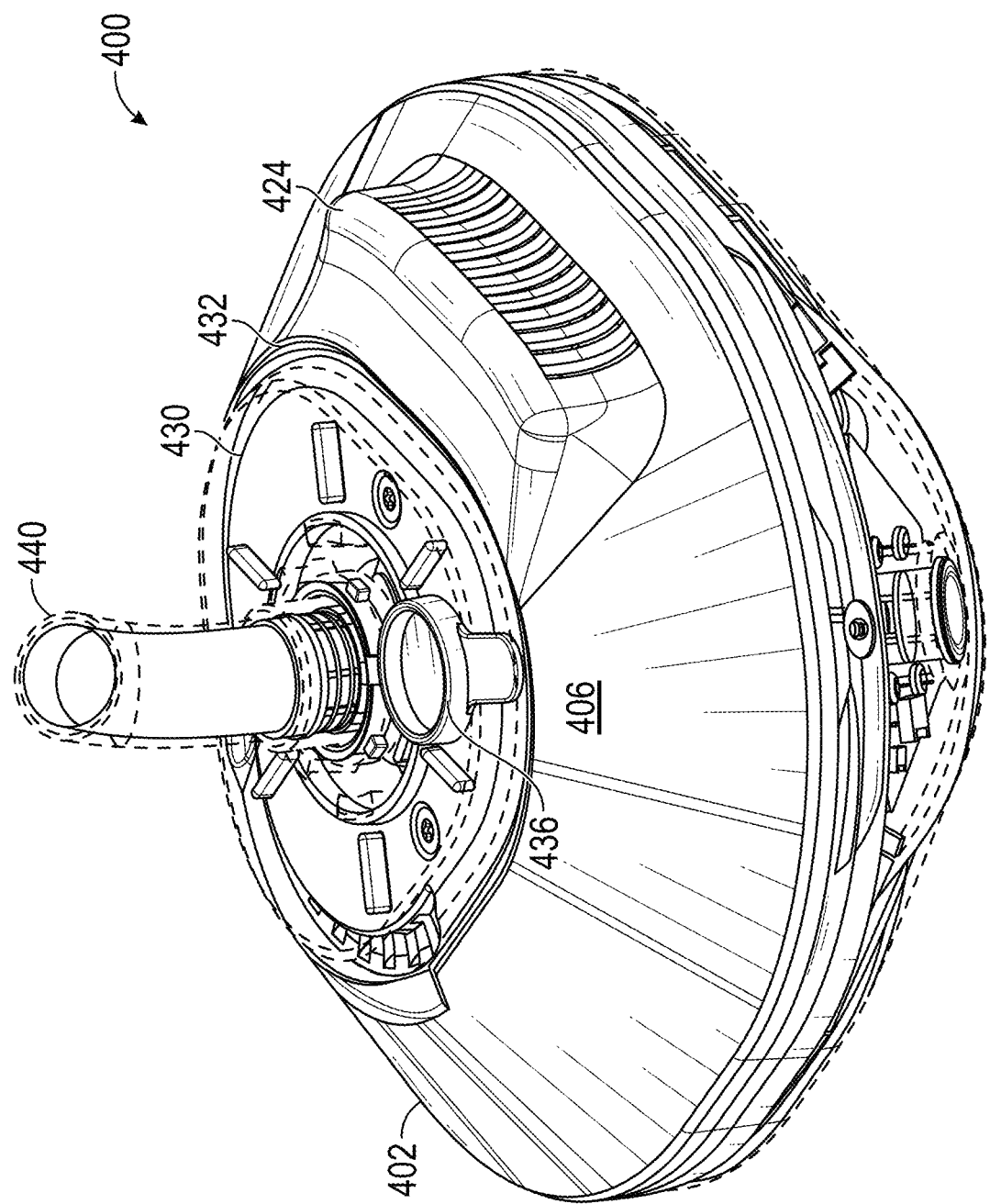
FIG. 5 shows a perspective view of another embodiment of the presently disclosed gas irradiation apparatus having a cooling air intake in the housing.
Figure 6:
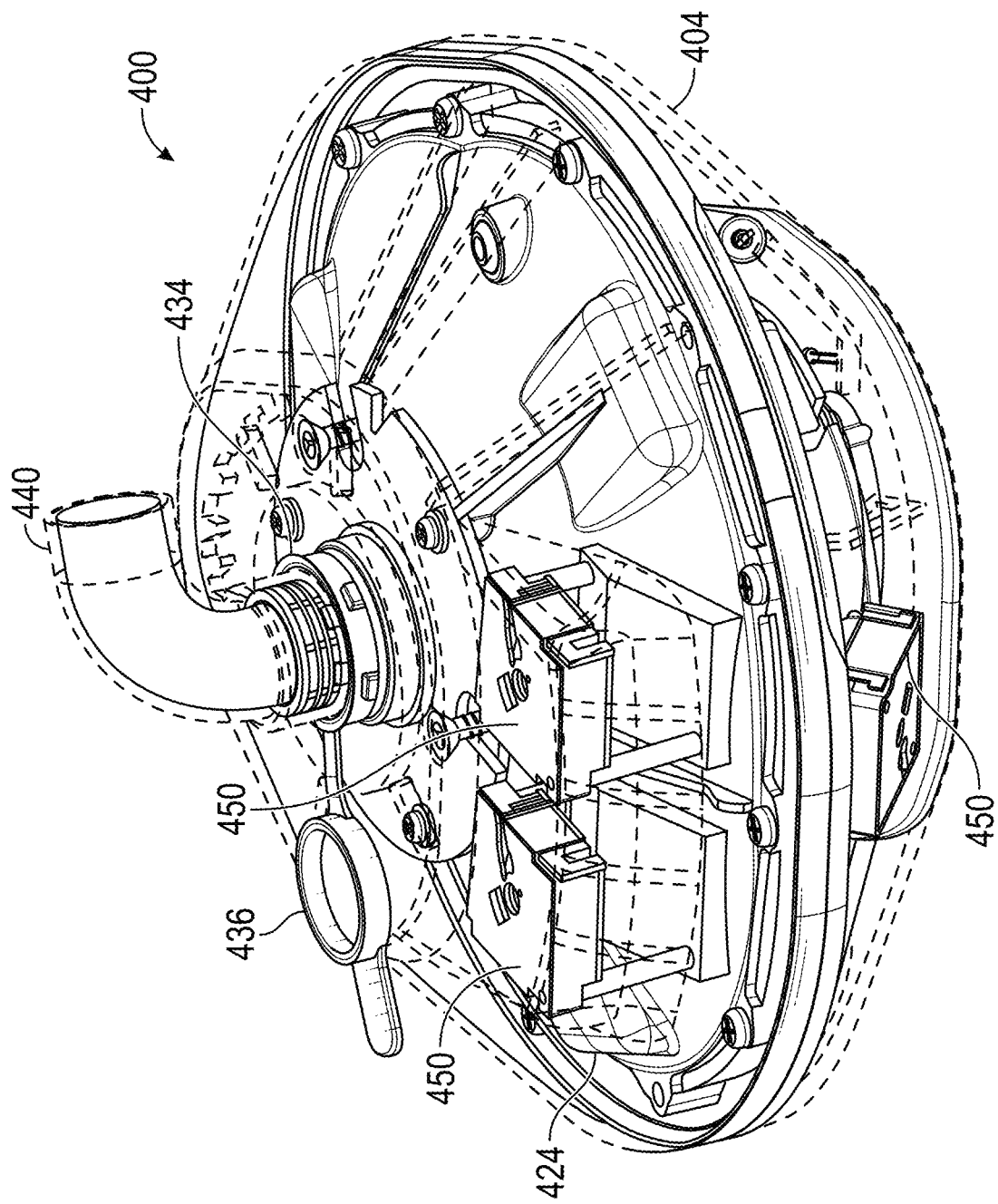
FIG. 6 shows a view of the embodiment of FIG. 5, showing an option for positioning of internal cooling fans.

FIGS. 5-6 show an embodiment of the device 400 with a view directed toward the gas outlet side of an embodiment of the apparatus with breathing hose module 430 deposed within gas outlet cavity portion 432 of second housing member 406. FIGS. 5-6 show an embodiment of a hose access cover 436 which snaps over breathing hose receptacle 434 when hose attachment member 440 is disconnected from the breathing hose receptacle.

In the embodiment of the device 400 depicted in FIGS. 5-6, second housing member 406 may have an air intake 424 through which cooling air is drawn into housing assembly 402 by one or more cooling fans 450. Air intake 424 may be utilized instead of, or in addition to, the cooling gas intakes 124 shown in FIG. 2. Cooling fans 450 may be positioned directly below air intake 424 as shown in FIG. 6 and also within first housing member 404. It is to be appreciated that except for the distinctions indicated within the preceding two paragraphs, the embodiment of the device 400 depicted in FIGS. 5-6, utilizes the same components as discussed for the embodiment of the device 100 depicted in FIGS. 1-4 and as disclosed in FIGS. 7-11 and functions in the same manner. It therefore should be understood that the discussion hereafter pertains to both devices 100, 400 but, for the sake of simplicity, the item numbers referenced hereinafter shall be those utilized in describing device 100.

When the irradiation apparatus 100 is in a normal flow configuration, treated gas is discharged through the breathing hose receptacle 134 to a breathing hose and mask. As shown in the detail of FIG. 16, exhaust seals 138 may be disposed between the housing assembly 102 and the irradiation chamber to prevent any cooling gas to enter into the gas outlet of breathing hose receptacle 134.

As described above, the housing assembly 102 may have cavity portions which are configured to receive modules which are respectively disposed into the cavity portions of the first housing member 104 and the second housing member 106. A filter module 112 may be disposed within a gas inlet cavity portion 114 of the first housing member 104 with the filter module connected to the gas inlet 122. A breathing hose module 130 may be disposed within the gas outlet cavity portion 132 of the second housing member 106 with the breathing hose module connected to the gas outlet.

Alternatively, to provide a reverse flow configuration, the breathing hose module 130 may be disposed within the gas inlet cavity portion 114 of the first housing member 104 with the breathing hose module connected to the gas inlet 122. In this configuration, which may be utilized to purify the exhalations of a person infected with a disease or virus, an embodiment of a breathing hose module 130 may be utilized which is configured to receive a filter, so that the exhalations are filtered prior to being introduced into the irradiation chamber. While a filter module 112 may be disposed within the gas outlet cavity portion of the second housing member 106, the filter would be filtering gas which has already been irradiated and may therefore be omitted. The modules 112, 130 may be configured to be retained within the cavity portions of the housing members with fastening means, such as screws, or with fast connectors such as snap latches, draw latches, rotary draw latches, etc. with seal elements between the modules and cavity portions.

Figure 16:
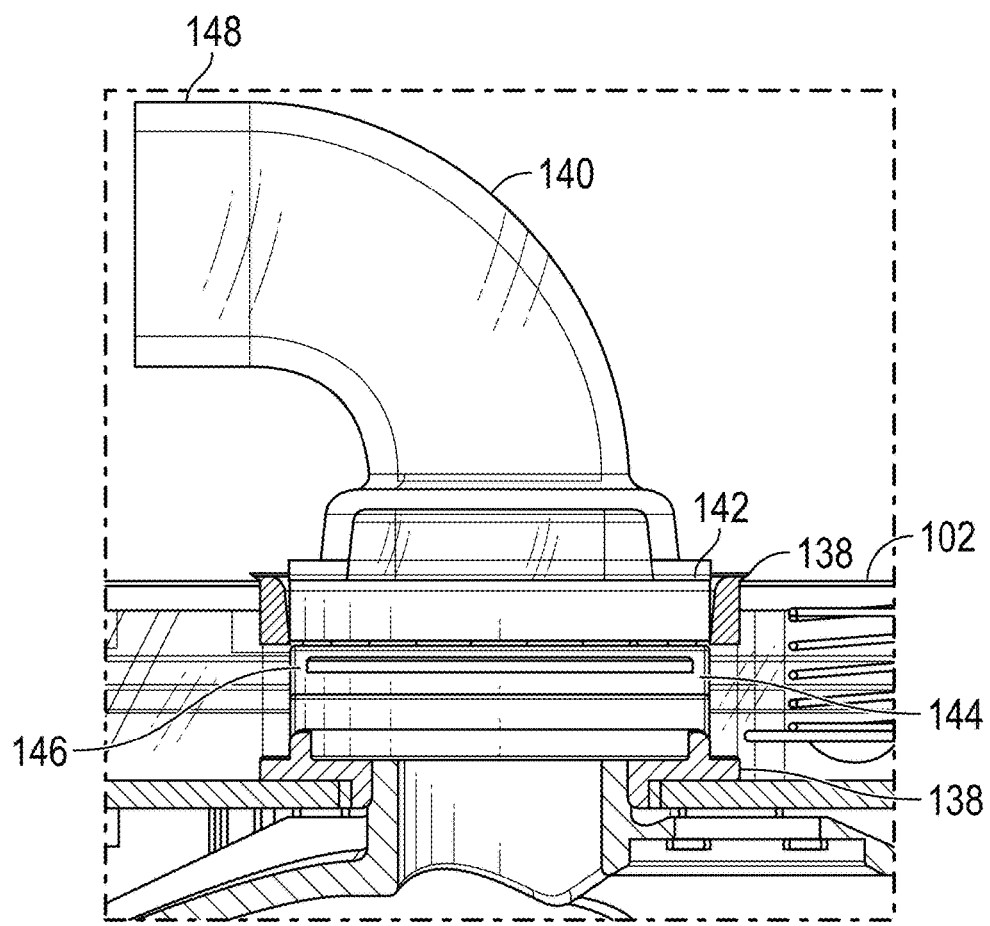
FIG. 16 shows exhaust seals between the outer housing and the outlet of the reaction chamber.

As shown FIG. 7 and in the detailed view of FIG. 16, a hose attachment member 140, such as molded hose elbow, may be utilized to connect a breathing hose to the breathing hose receptable 134. The hose attachment member 140 may have an integrated seal 142 at its base which mates with the breathing hose receptacle 134. The base may have an integrated magnet 144 which attaches to a mating steel ring 146 or magnet contained within the breathing hose receptacle 134. The magnet 144 may be utilized in conjunction with a sensor which detects whether a breathing hose has been attached to the breathing hose receptacle 134. The hose attachment member 140 may have an exterior end 148 for receiving an industry standard 15 millimeter CPAP hose. The hose attachment member 140 may be configured to provide 360 degrees of rotation within the breathing hose receptacle 134. A silicon/elastomer seal may be utilized to provide an airtight connection between the base of the hose attachment member 140 and the breathing hose receptacle 134.

Figure 18:
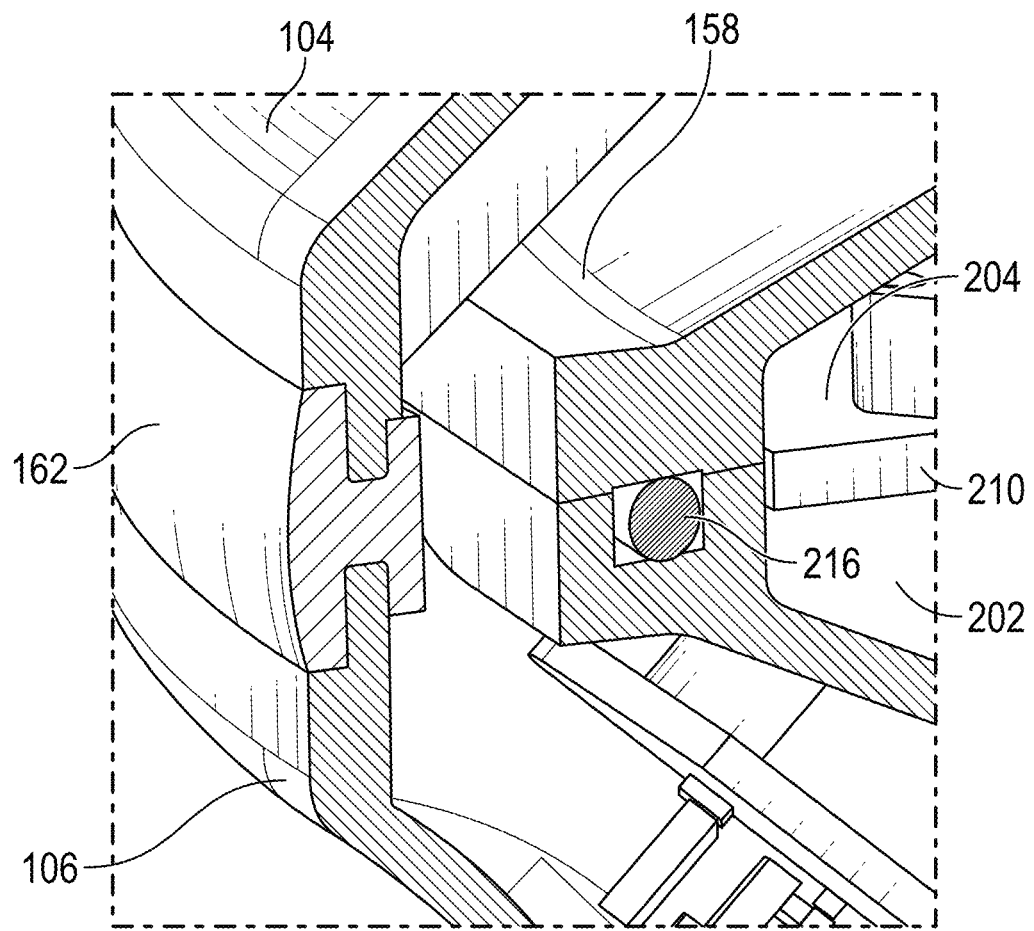
FIG. 18 shows the exterior housing may be sealed by a band seal between the first housing member and the second housing member.

FIG. 7 depicts an exploded view of an embodiment of the presently disclosed gas irradiation apparatus 100, showing the relative positions of the components of the apparatus. As shown in FIG. 7, housing assembly 102 comprises a first housing member 104 and a second housing member 106. First housing member 104 has an open proximate end defined by a peripheral edge 150. Opposite the open proximate end, first housing member 104 has a closed distal end 152 Likewise, second housing member 106 has an open proximate end defined by peripheral edge 154 and a closed distal end 156. Housing assembly 102 is configured such that when the first housing member 104 and second housing member 106 are attached together at the respective peripheral edges 150, 154, a generally spherical or ellipsoidal encasement is formed which encloses the irradiation chamber assembly 200, which comprises first chamber 202 and second chamber 204 as depicted in FIG. 8. The attachment of the first housing member 104 and the second housing member 106 may be made with either a fused connection or a detachable connection. With the detachable connection, a double face seal 162 as shown in FIGS. 18-19 may be disposed between the adjacent peripheral edges to provide the airtight seal.

Figure 15:
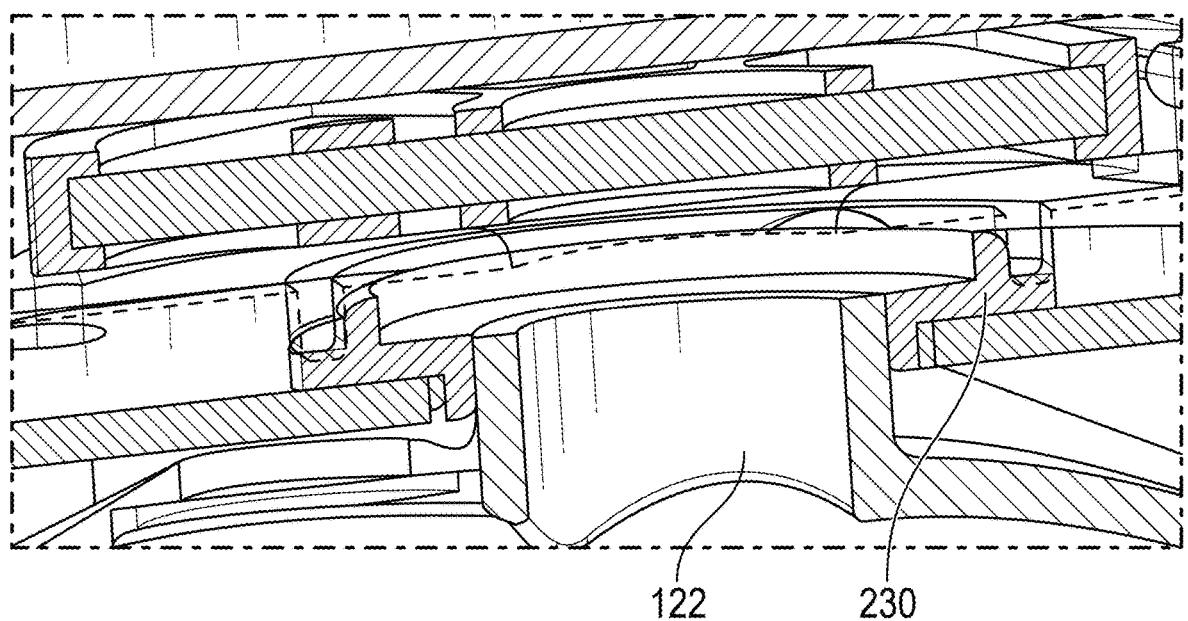
FIG. 15 shows an intake seal between the outer housing and the inlet to the reaction chamber.

As shown in FIG. 7, gas inlet cavity portion 114 is formed between the interior surface 158 of the first housing member 104 and the outside surface 206 of the first chamber 202 of the irradiation chamber assembly wherein the gas inlet 122 extends from the closed distal end 152 of the first housing member 104 and extends into the interior of the first chamber 202 of the irradiation chamber assembly 200. Gas outlet cavity portion 132 is formed between the interior surface 160 of the second housing member 106 and the outside surface 208 of the second chamber 204 of the irradiation chamber assembly 200 wherein the gas outlet extends outwardly from the interior of the second chamber 204 of the irradiation chamber assembly 200 to the closed distal end 156 of the second housing member 106. As shown in FIG. 15, there are intake airway seals 230.

Figure 11:
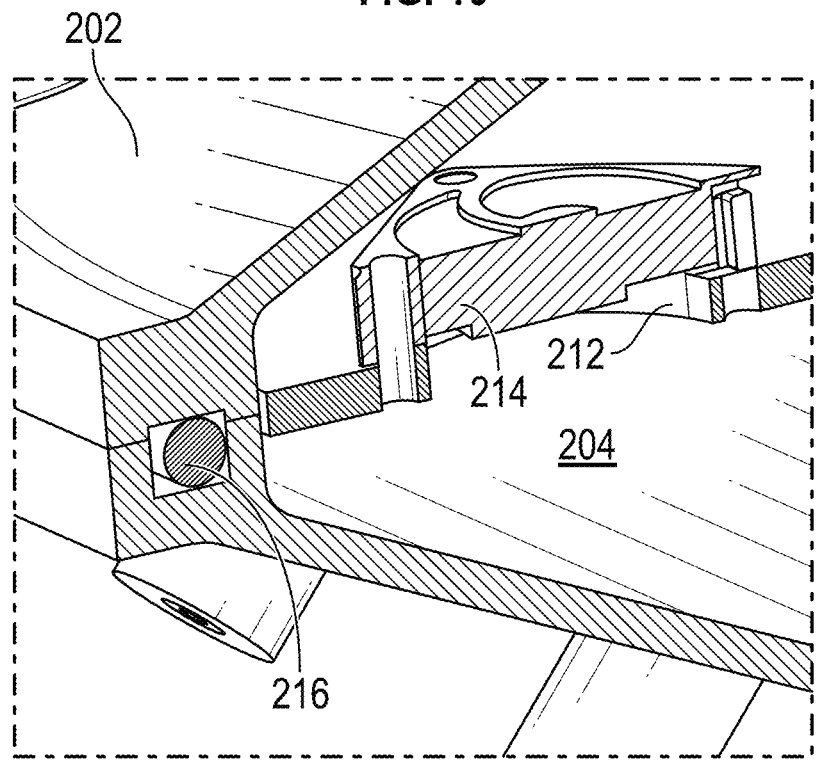
FIG. 11 shows a detailed view of a double face seal between the first chamber and the second chamber.

FIG. 8 shows a sectional view of irradiation chamber assembly 200 showing first chamber 202, second chamber 204 and intermediate wall 210 which separates the first chamber and the second chamber. As shown in FIG. 9, one or more conduits 212 extend between first chamber 202 and second chamber 204. It is to be appreciated that the irradiation chambers 202, 204 are sealed to insure that the one or more conduits 212 are the exclusive flow path between first chamber 202 and second chamber 204. For example, as shown in FIG. 11, sealing element 216 provides an O-ring double face seal between the first chamber 202 and the second chamber 204. FIG. 15 depicts an intake airway seal 230 between the housing assembly 102 and the gas inlet to the first chamber 202.

As shown in FIGS. 8, 9, 9A and 11, a gas transfer fan 214 is disposed in each of the one or more conduits 212, where the gas transfer fan creates a pressure differential between the first chamber 202 and the second chamber 204 and thereby induces a flow of gas between the first chamber and the second chamber. In normal flow operation, the pressure differential will cause flow from the first chamber 202 into the second chamber 204. In reverse flow operation, the fan direction may be reversed by operation of system controller 300. However, as indicated above, a "reverse flow operation" may also be achieved by disposing the breathing hose module 130 within the gas inlet cavity portion 114 of the first housing member 104 with the breathing hose module connected to the gas inlet 122 and, if desired, the filter module 112 may be disposed within the gas outlet cavity portion 132 of the second housing member 106 with the filter module connected to the beathing hose receptacle 134.

Figure 10:
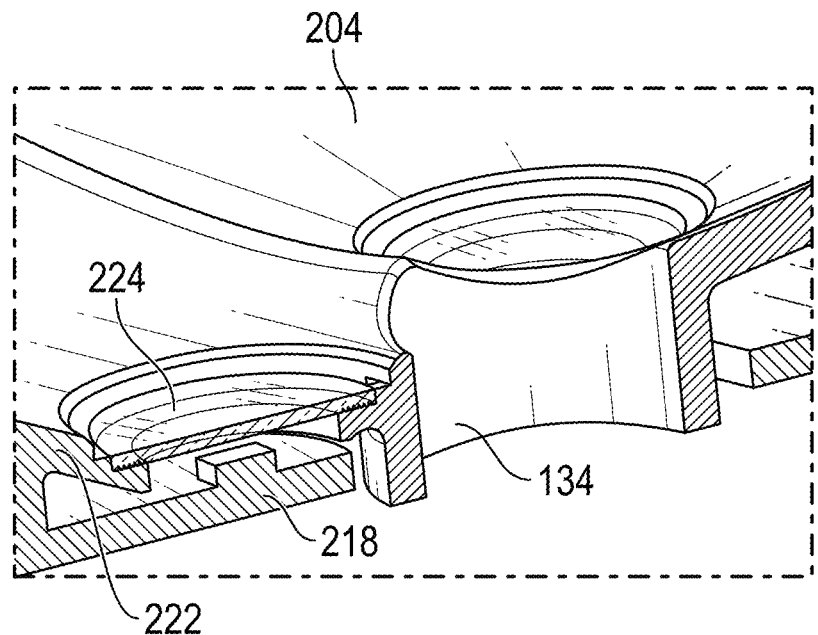
FIG. 10 shows a detailed view of a light source disposed within a light chamber.

The irradiation process of the irradiation chamber assembly is done by an array of light emitting diodes 218 which are configured to provide UVC light radiation into one or both chambers 202, 204 of irradiation chamber assembly 200. In one embodiment, the array of light emitting diodes 218 may comprise a first plurality of light emitting diodes providing UVC light into the first chamber 202 and a second plurality of light emitting diodes provided UVC light into the second chamber 204. The light emitting diodes 218 may be disposed on heat sink plates 220 which are positioned adjacent one or both chambers 202, 204. Cooling air is provided to heat sink plates 220 by cooling fans 250 and/or 450 as discussed above. As shown in FIG. 10, second chamber 204 may have a second chamber wall 222 which comprises one or more fused silica quartz windows 224, where a light emitting diode 218 is positioned adjacent the fused silica quartz window. Second chamber wall 222 may have comprise a reflective material. Likewise, first chamber 202 may have a first chamber wall 228 which comprises one or more fused silica quartz windows 224, where a light emitting diode 218 is positioned adjacent the fused silica quartz window. First chamber wall may further comprise a reflective material.

Figure 20:
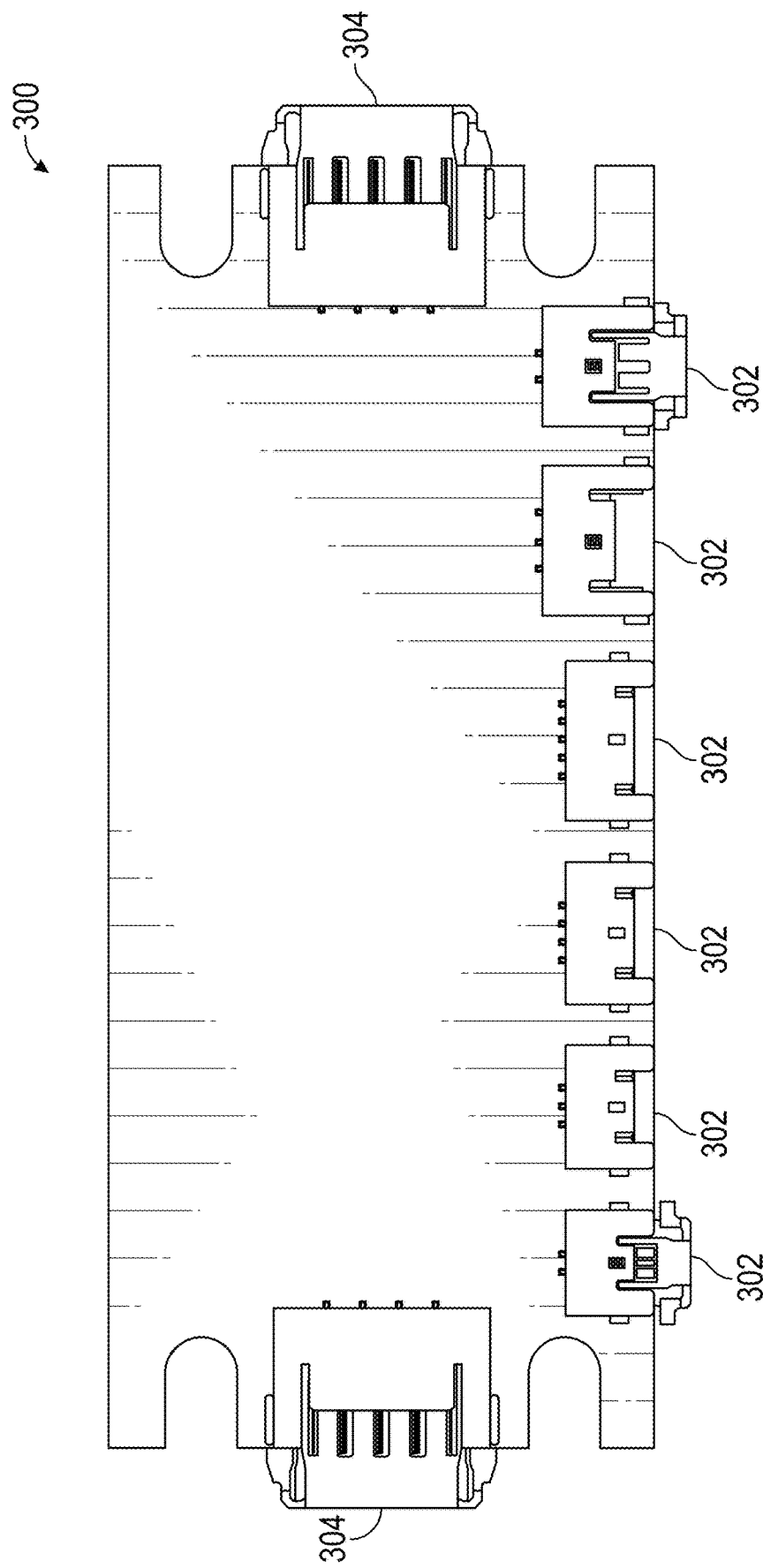
FIG. 20 shows an embodiment of a system controller which provides individual connectors for each system of the apparatus.

The systems of the gas irradiation apparatus are controlled by system controller 300 depicted in FIG. 20. The system controller has individual connectors 302 for each system interconnect, with the systems comprising the HEPA filter placement detector, the filter door status detector, gas transfer fan control, cooling fan control, and the hose placement detector. The controller 300 also comprises connectors 304 which are utilized to actuate and control the arrays of light emitting diodes 218. The light emitting diodes 218 are disposed on thermal management printed circuit boards, such as SINKPAD, for heat dissipation.

Having thus described the preferred embodiment of the invention, what is claimed as new and desired to be protected by Letters Patent includes the following:

1. A gas irradiation apparatus comprising:
a housing assembly comprising a gas inlet and a gas outlet;
an irradiation chamber assembly comprising a first chamber and an adjacent second chamber, the irradiation chamber assembly disposed within the housing assembly, the irradiation chamber connected to the gas inlet and the gas outlet;
an intermediate wall which spans across an interior of the irradiation chamber assembly thereby dividing the first chamber from the second chamber, the intermediate wall comprising a circumferential edge which seals against an inside surface of the irradiation chamber assembly, the intermediate wall comprising a conduit extending between the first chamber and the second chamber, the conduit being an exclusive flow path for a flow of gas between the first chamber and the second chamber;
a gas transfer fan disposed within the conduit, the gas transfer fan configured to create a pressure differential between the first chamber and the second chamber and thereby induce a flow of a gas between the first chamber and the second chamber through the conduit;
an array of light emitting diodes disposed on a heat sink, the array of light emitting diodes configured to provide UVC light radiation into the irradiation chamber assembly; and
an auxiliary cooling fan disposed within a cavity between an exterior of the irradiation chamber assembly and an interior wall of the housing assembly, the auxiliary cooling fan adjacent a cooling gas intake, the auxiliary cooling fan configured to draw a cooling gas through the cooling gas intake and direct the cooling gas over the array of light emitting diodes and the heat sink, wherein the cooling gas intake and the exterior of the irradiation chamber assembly are configured so that the cooling gas is prevented from entering an interior of the irradiation chamber assembly and mixing with any gas which has entered the interior of the irradiation chamber assembly.

2. The gas irradiation apparatus of claim 1 wherein the array of light emitting diodes comprises a first plurality of light emitting diodes configured to provide UVC light into the first chamber and a second plurality of light emitting diodes configured to provide UVC light into the second chamber.

3. The gas irradiation apparatus of claim 2 wherein the first plurality of light emitting diodes are disposed within a first heat sink plate positioned adjacent the first chamber and the second plurality of light emitting diodes are disposed within a second heat sink plate positioned adjacent the second chamber.

4. The gas irradiation apparatus of claim 3 wherein the first chamber comprises a first chamber wall comprising a first plurality of fused silica quartz windows, wherein each of the light emitting diodes of the first plurality of light emitting diodes is positioned adjacent to a corresponding fused silica quartz window of the first plurality of fused silica quartz windows.

5. The gas irradiation apparatus of claim 3 wherein the second chamber comprises a second chamber wall comprising a second plurality of fused silica quartz windows, wherein each of the light emitting diodes of the second plurality of light emitting diodes is positioned adjacent to a corresponding fused silica quartz window of the second plurality of fused silica quartz windows.

6. The gas irradiation apparatus of claim 1 wherein the housing assembly comprises a first housing member and a second housing member.

7. The gas irradiation apparatus of claim 6 wherein the first housing member comprises a first proximate end having a first peripheral edge and the second housing member comprises a second proximate end having a second peripheral edge, the first peripheral edge and the second peripheral edge configured to be attached together in opposite facing relation and form an airtight seal.

8. The gas irradiation apparatus of claim 7 wherein a double face seal is disposed between the first peripheral edge and the second peripheral edge.

9. The gas irradiation apparatus of claim 6 wherein the first housing member comprises a first housing member distal end comprising a gas inlet cavity portion through which the gas inlet extends.

10. The gas irradiation apparatus of claim 9 wherein the gas inlet cavity portion is configured to receive a filter module, the filter module comprising a filter seat configured to receive a filter element.

11. The gas irradiation apparatus of claim 10 wherein a filter module cover is pivotally attached to the filter module, the filter module cover configured to secure the filter element within the filter seat and allow an incoming flow of gas to flow through the filter element and into the gas inlet.

12. The gas irradiation apparatus of claim 11 comprising a sensor configured to detect when the filter element is disposed in the filter seat.

13. The gas irradiation apparatus of claim 11 comprising a sensor configured to detect when the filter module cover is in a closed position.

14. The gas irradiation apparatus of claim 6 wherein the second housing member comprises a second housing member distal end comprising a gas outlet cavity portion through which the gas outlet discharges a treated gas.

15. The gas irradiation apparatus of claim 14 wherein the gas outlet cavity portion is configured to receive a breathing hose module, the breathing hose module comprising a breathing hose receptacle.

16. The gas irradiation apparatus of claim 15 wherein the breathing hose module comprises a protection door to close over the breathing hose receptacle.

17. The gas protection apparatus of claim 16 wherein the protection door is biased to close when a breathing hose is not attached to the breathing hose receptacle.

18. The gas irradiation apparatus of claim 1 wherein the irradiation chamber assembly comprises a volume ranging from 400 to 600 milliliters.

19. The gas irradiation apparatus of claim 1 wherein the irradiation chamber assembly comprises an interior surface comprising a reflective material.

20. A gas irradiation apparatus comprising:
a housing assembly comprising a first housing member and a second housing member, wherein the first housing member comprises a gas inlet cavity portion through which a gas inlet extends, wherein the gas inlet cavity portion is configured to receive a breathing hose module comprising a breathing hose receptacle and a manually positionable protection door to close over the breathing hose receptacle and the second housing member comprises a gas outlet cavity portion through which a gas outlet discharges a treated gas;
an irradiation chamber assembly comprising a first chamber and an adjacent second chamber, the irradiation chamber assembly disposed within the housing assembly;
an intermediate wall separating the first chamber from the second chamber, wherein the intermediate wall comprises a conduit extending between the first chamber and the second chamber, the conduit being an exclusive flow path a flow of gas between the first chamber and the second chamber;
a gas transfer fan disposed within the conduit, the gas transfer fan configured to create a pressure differential between the first chamber and the second chamber and thereby induce a flow of a gas between the first chamber and the second chamber through the conduit; and
an array of light emitting diodes disposed within the irradiation chamber assembly configured to provide UVC light radiation into the irradiation chamber assembly.

21. The gas irradiation apparatus of claim 20 wherein the gas inlet cavity portion is configured to receive a filter module, the filter module comprising a filter seat configured to receive a filter element, the filter module further comprising a filter module cover pivotally attached to the filter module, the filter module cover configured to secure the filter element within the filter seat and allow an incoming flow of gas to flow through the filter element, and wherein the gas outlet cavity portion is configured to receive a breathing hose module comprising a breathing hose receptacle and a manually positionable protection door to close over the breathing hose receptacle.

* * * * *